US012797414B2

(12) United States Patent
Muller

(10) Patent No.: US 12,797,414 B2

(45) Date of Patent: Nov. 17, 2026

(54) EYE TREATMENTS EMPLOYING SERUM FROM WHOLE BLOOD

(71) Applicant: David Muller, Boston, MA (US)

(72) Inventor: David Muller, Boston, MA (US)

(73) Assignee: David Muller, Boston, MA (US)

( * ) Notice: Subject to any disclaimer, the term of this patent is extended or adjusted under 35 U.S.C. 154(b) by 738 days.

(21) Appl. No.: 17/086,454

(22) Filed: Nov. 1, 2020

(65) Prior Publication Data

US 2021/0046111 A1 Feb. 18, 2021

Related U.S. Application Data

(63) Continuation-in-part of application No. PCT/US2019/030228, filed on May 1, 2019.

(60) Provisional application No. 62/967,572, filed on Jan. 29, 2020, provisional application No. 62/733,918, filed on Sep. 20, 2018, provisional application No. 62/664,939, filed on May 1, 2018.

(51) Int. Cl.
*A61K 35/16* (2015.01)
*A61K 9/00* (2006.01)
*A61K 31/728* (2006.01)
*A61K 38/13* (2006.01)

(52) U.S. Cl.
CPC ............ *A61K 35/16* (2013.01); *A61K 9/0048* (2013.01); *A61K 38/13* (2013.01)

(58) Field of Classification Search
CPC ...... A61K 35/16; A61K 9/0048; A61K 38/13; A61K 31/728; A61K 47/46
See application file for complete search history.

(56) References Cited

U.S. PATENT DOCUMENTS

| | | | |
|---|---|---|---|
| 2018/0050064 A1 | 2/2018 | Schrott et al. | |
| 2019/0008764 A1 | 1/2019 | Askew | |

FOREIGN PATENT DOCUMENTS

| | | | |
|---|---|---|---|
| CN | 205275172 U | 6/2016 | |
| FR | 2696756 | 12/1994 | |
| KR | 20120022574 | 3/2012 | |
| LT | 2016506 | 9/2016 | |
| WO | WO 2018104950 A1 * | 6/2018 | .......... A61K 31/167 |

OTHER PUBLICATIONS

Chiang C.-C. et al., "Allogeneic serum eye drops for the treatment of persistent corneal epithelial defect", Eye (2009), vol. 23, pp. 290-293. (Year: 2009).*

Abuhanoglu G. et al., "Radiation sterilization of new drug delivery systems", Review—Interventional Medicine & applied Science (2014), vol. 6, No. 2, pp. 51-60. (Year: 2014).*

Park Y. et al., "A Randomized Multicenter Study Comparing 0.1%, 0.15%, and 0.3%Sodium Hyaluronate with 0.05% Cyclosporine in the Treatment of Dry Eye", Journal of Ocular Pharmacology and Therapeutics, vol. 33, No. 2 ( 2017); https://doi.org/10.1089/jop.2016.0086 (total pp. 11). (Year: 2017).*

Zyl et al., "Pooling Strategies to Reduce the Cost of HIV-1 RNA Load Monitoring in a Resource-Limited Setting", Clinical Infectious Diseases, 2011, vol. 52, No. 2, pp. 264-270. (Year: 2011).*

U2—Semeraro et al., "Evaluation of the Efficacy of 50% Autologous Serum Eye Drops in Different Ocular Surface Pathologies", BioMed Research International, vol. 2014, Article ID 826970, 11 pages (http://dx.doi.org/10.1155/2014/826970). (Year: 2014).*

V2—CDC: Blood Safety Basics, published online on Aug. 23, 2011 at the website—https://www.cdc.gov/bloodsafety/basics.html (total pp. 2) (Year: 2011).*

W2—Tseng C-L et al., "Synergic effect of artificial tears containing epigallocatechin gallate and hyaluronic acid for the treatment of rabbits with dry eye syndrome", PLoS ONE 11(6): e0157982; pp. 1-18 (doi: 10.1371/journal.pone.0157982). (Year: 2016).*

Tuck et al., "Standard Operating Procedures for Serum and Plasma Collection: Early Detection Research Network Consensus Statement Standard Operating Procedure Integration Working Group", J. Proteome Res., Jan. 2009, vol. 8(1), pp. 113-117; doi: 10.1021/pr800 (Year: 2009).*

Isman FK. et al., "Evaluation of serum hyaluronic acid level and hyaluronidase activity in acute and chronic hepatitis C", The Journal of International Medical Research, 2007, vol. 35, pp. 346-352. (Year: 2007).*

Nakamura S. et al., "Protective Effect of D—Hydroxybutyrate on Corneal Epithelia in Dry Eye Conditions through Suppression of Apoptosis", IOVS, Nov. 2003, vol. 44, No. 11, pp. 4682-4688. (Year: 2003).*

Versteegen R. et al., "Gamma Irradiation of Animal Serum: An Introduction", BioProcessing Journal: Trends & Developments in Bioprocess Technology, Summer 2016, vol. 15, No. 2, pp. 5-11. (Year: 2016).*

"Blood Collection" by B. Armstrong, published by Blackwell Publishing Ltd. in ISBT Science Series (2008) 3, 123-136 (14 pages).

Lallemand F. et al, "Cyclosprine A delivery to the eye: A pharmaceutical challenge," European Journal of Pharmaceutics and Biopharmaceutics, Elsevier Science Publishers B.V., vol. 56, No. 3, Nov. 1, 2003, pp. 307-318.

Extended European Search Report by the European Patent Office for EP Appl. No. 19796766.4, dated Feb. 2, 2025 (8 pages).

Meer et al., "Quality standards, safety and efficacy of blood-derived serum eye drops: A review", Transfusion and Apheresis Science 54 (2016), pp. 164-167.

Tomida I. et al., "Cannabinoids and glaucoma", Br. J. Ophthalmol, 2004, 88(5) p. 708-713.

(Continued)

*Primary Examiner* — Satyendra K Singh

(74) *Attorney, Agent, or Firm* — McDonnell Boehnen Hulbert & Berghoff LLP

(57) ABSTRACT

Eye drops for treating dry eye include serum extracted from whole blood. An example method includes collecting whole blood from one or more donors (e.g., allogenic whole blood); separating the whole blood to obtain a serum; applying radiation to the serum for viral inactivation; and adding one or more additives to the serum to produce eye drops.

18 Claims, 1 Drawing Sheet

(56) References Cited

OTHER PUBLICATIONS

International Search Report and Written Opinion issued by the Federal Institute of Industrial Property for Int'l Appl. No. PCT/US2021/015747, dated May 13, 2021 (7 pages).
International Preliminary Report on Patentability issued by the Federal Institute of Industrial Property for Int'l Appl. No. PCT/US2019/030228 dated May 1, 2018 (5 pages).
European Examination Report by the European Patent Office for EP Appl. No. 19796766.4, dated Jun. 17, 2025 (9 pages).

* cited by examiner

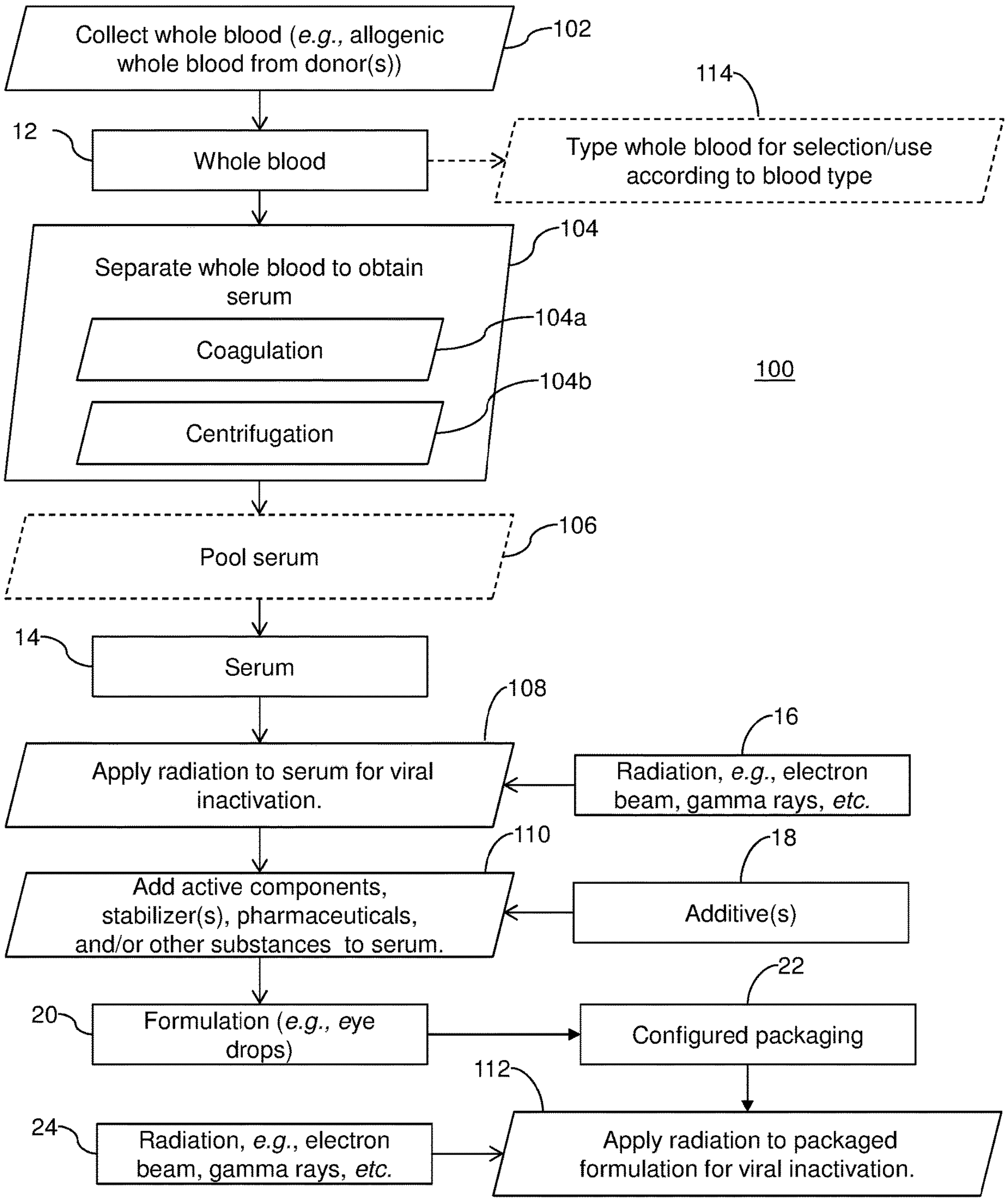
Collect whole blood (*e.g.,* allogenic whole blood from donor(s))
102
114
12
Whole blood
Type whole blood for selection/use according to blood type
104
Separate whole blood to obtain serum
104a
Coagulation
104b
Centrifugation
100
106
Pool serum
14
Serum
108
16
Apply radiation to serum for viral inactivation.
Radiation, *e.g.*, electron beam, gamma rays, *etc.*
110
18
Add active components, stabilizer(s), pharmaceuticals, and/or other substances to serum.
Additive(s)
22
20
Formulation (*e.g., eye* drops)
Configured packaging
112
24
Radiation, *e.g.*, electron beam, gamma rays, *etc.*
Apply radiation to packaged formulation for viral inactivation.

EYE TREATMENTS EMPLOYING SERUM FROM WHOLE BLOOD

CROSS REFERENCE TO RELATED APPLICATIONS

This application is a continuation-in-part application of International Patent Application No. PCT/US2019/030228, filed May 1, 2019, which claims priority to and the benefit of U.S. Provisional Patent Application No. 62/664,939, filed May 1, 2018, and U.S. Provisional Patent Application No. 62/733,918, filed Sep. 20, 2018. This application also claims priority to and the benefit of U.S. Provisional Patent Application No. 62/967,572, filed Jan. 29, 2020. The contents of all above applications are incorporated entirely herein by reference.

BACKGROUND

Field

The present disclosure pertains to eye treatments, and more particularly, to eye treatments (e.g., for dry eye) that employ serum-based formulations.

Description of Related Art

Dry eye occurs when the quantity and/or quality of tears fails to keep the surface of the eye adequately lubricated. In a healthy eye, lubricating tears called basal tears continuously bathe the cornea. With every blink of the eye, basal tears flow across the cornea, nourishing its cells and providing a layer of liquid protection against the environment. When the glands nearby each eye fail to produce enough basal tears, or when the composition of the tears changes, the health of the eye and vision are compromised. Vision may be affected, for instance, because tears on the surface of the eye play an important role in focusing light.

Tears are a complex mixture of fatty oils, water, mucus, and more than 1500 different proteins that keep the surface of the eye smooth and protected from the environment, irritants, and infectious pathogens. Tears include three layers:

- an outer, oily lipid layer, produced by the Meibomian glands, keeps tears from evaporating too quickly and helps tears remain on the eye;
- a middle aqueous layer, including lacrimal fluid produced by the main and accessory lacrimal glands, provides a watery physiologic saline to moisten and nourish the conjunctiva and cornea;
- an inner mucin layer, produced by goblet cells, binds water from the aqueous layer to ensure that the eye remains wet.

Artificial tear substitutes in the form of eye drops, eye gel, or eye spray are offered for treating dry eye. Artificial tear substitutes, however, might contain only some components of natural tears, and as such, might not provide a sustainable treatment for dry eye.

SUMMARY

According to the present disclosure, eye drops for treating dry eye include serum extracted from whole blood. Advantageously, serum-based eye drops are biomechanically and biochemically similar to lacrimal fluid in the aqueous layer of tears. In contrast to artificial tears in current use, serum-based eye drops provide a more sustainable treatment for dry eye.

In some cases, serum eye drops may be produced from autologous whole blood, i.e., whole blood obtained from the patient to be treated. In other cases, serum eye drops may be produced from allogeneic whole blood, i.e., whole blood obtained from a donor who is not the patient to be treated. The use of allogeneic whole blood allows a patient who cannot provide his or her own whole blood to be treated with serum eye drops. A supply of eye drops for treating dry eye can be more conveniently produced and delivered to patients without requiring the patients to provide their own whole blood.

According to aspects of the present disclosure, an example method includes collecting whole blood from one or more donors (e.g., allogeneic whole blood); separating the whole blood to obtain a serum; applying radiation to the serum for viral inactivation; and adding one or more additives to the serum to produce eye drops.

The example method may further include selecting the whole blood from the one or more donors according to blood type.

In the example method, separating the whole blood serum may include coagulating the whole blood and centrifuging the whole blood.

The example method may further include pooling the serum from a plurality of donors to produce a desired volume of eye drops.

In the example method, the radiation may be corpuscular radiation and/or electromagnetic radiation.

The example method may further include testing the whole blood for particular viruses.

The example method may further include applying additional radiation to the serum and/or the eye drops to reduce a level of active biological contaminants or pathogens.

In the example method, separating the whole blood to obtain the serum may result in separation of cellular components from the serum.

In the example method, the one or more additives may supplement active components in the serum according to particular concentrations.

In the example method, the one or more additives may include one or more stabilizers that allow the eye drops to be stably stored at particular temperatures.

In the example method, the one or more additives may include one or more pharmaceuticals (e.g., cyclosporine).

In the example method, the one or more additives (e.g., saline and/or hyaluronic acid) may determine a viscosity of the eye drops.

The example method may further include storing the eye drops in packaging (e.g., single dose containers). In this case, the example method may further include applying additional radiation to the stored eye drops for viral inactivation.

The example method may further include combining the eye drops with a medium that dissolves in an eye over time and releases the eye drops in a controlled and time-dependent manner.

One or more steps of the method may employ low temperature to slow degradation of the whole blood, serum, and/or eye drops.

BRIEF DESCRIPTION OF THE DRAWINGS

FIG. 1 illustrates an example process for producing a formulation (e.g., implemented as eye drops) from whole blood for a treatment (e.g., of dry eye), according to aspects of the present disclosure.

While the present disclosure is susceptible to various modifications and alternative forms, a specific embodiment thereof has been shown by way of example in the drawings and will herein be described in detail. It should be understood, however, that it is not intended to limit the present disclosure to the particular forms disclosed, but on the contrary, the intention is to cover all modifications, equivalents, and alternatives falling within the spirit of the present disclosure.

DESCRIPTION

According to the present disclosure, eye drops for treating dry eye include serum extracted from whole blood. Advantageously, serum-based eye drops are biomechanically and biochemically similar to lacrimal fluid in the aqueous layer of tears. In contrast to artificial tears in current use, serum-based eye drops provide a more sustainable treatment for dry eye.

In some cases, serum eye drops may be produced from autologous whole blood, i.e., whole blood obtained from the patient to be treated. In other cases, serum eye drops may be produced from allogeneic whole blood, i.e., whole blood obtained from a donor who is not the patient to be treated. The use of allogeneic whole blood allows a patient who cannot provide his or her own whole blood to be treated with serum eye drops. A supply of eye drops for treating dry eye can be more conveniently produced and delivered to patients without requiring the patients to provide their own whole blood.

FIG. 1 illustrates an example process 100 for producing a serum-based formulation 20 from allogeneic whole blood 12. The formulation 20 can be implemented as eye drops or another type of treatment. In some cases, the formulation 20 may be employed for treatment of dry eye. In act 102, the whole blood 12 is collected. In act 104, the whole blood 12 is separated to obtain serum 14. The whole blood 12 may be separated, for instance, by a process including coagulation in act 104*a* and centrifugation in act 104*b*.

In some cases, the whole blood 12 may be allogeneic whole blood collected from one or more donors who are not the patient to be treated. As such, the allogeneic whole blood may be typed as A/B/AB/O+/− in act 114 so that the formulation 20 can be matched for use by patients according to blood type. To produce a desired supply of the formulation 20, allogeneic whole blood may be collected from a plurality of donors and the serum from each donor may be pooled in act 106 to provide the serum 14. Such pooling can provide a high volume of the formulation 20 for a plurality of doses and/or distribution to a plurality of patients For instance, a sufficient amount of serum 14 can be pooled from approximately sixteen donors, i.e., the process 100 can produce a sufficient amount of serum 14 from sixteen donors on average. However, it is understood that any number of donors may be employed to produce the volume of the formulation 20.

After the serum 14 has been separated from the rest of the allogeneic whole blood 12 and, if necessary, pooled, radiation 16 is applied to the serum 14 in act 108 for viral inactivation. The radiation 16 provides a sufficient dose of energy to render viruses (e.g., enveloped/non-enveloped, DNA/RNA-based, etc.) in the serum 14 inactive. The radiation 16 may be corpuscular, i.e., include beams of subatomic particles such as neutrons, electrons, and/or protons. Alternatively or additionally, the radiation 16 may be electromagnetic, e.g., include gamma rays. In some cases, the process 100 may include additional act(s) to test allogeneic whole blood from each donor for certain viruses. If necessary, the allogeneic whole blood from a particular donor may be excluded or processed in other ways to ensure that such viruses are not present in the serum 14.

Radiation may also be applied to sterilize the serum 14, i.e., reduce the level of active biological contaminants or pathogens. Although the whole blood 12 may be initially sterile and the acts of the process 100 may be conducted to preserve this sterility, a sterilizing process with radiation may be additionally employed during the process 100. For instance, a sterilizing process may be applied before viral inactivation in act 108. This sterilizing process may employ corpuscular radiation (e.g., beams of subatomic particles such as neutrons, electrons, and/or protons) or electromagnetic radiation (e.g., radio waves, visible/invisible light, infrared light, ultraviolet radiation, x-radiation, and/or gamma rays). The type and dose of radiation to achieve viral inactivation, however, may be different from sterilizing application of radiation. The sterilizing process may also employ sensitizers that enhance the sterilizing effect of the radiation on the biological contaminants or pathogens. Additionally or alternatively, sterilizing radiation may be applied at another point in the process, e.g., to sterilize the formulation 20.

Exposure to the radiation 16 does not unacceptably damage the serum 14. For instance, after act 104, cellular components are separated from the serum 14, so that only proteins remain in the serum 14 as active ingredients. Such proteins are not unacceptably denatured by electron beams, gamma rays, or other forms of the radiation 16. The application of the radiation 16 may also include the use of substances that can further minimize any damage to the serum 14.

Once viral inactivation has been achieved in act 108, one or more additives 18 may be added to the treated serum 14 in act 110. For instance, the serum 14 may include one or more active components that enhance the efficacy of the formulation 20, e.g., enhance healing effects associated with the serum 14 within the formulation 20. As such, certain active components in the serum 14 can be supplemented in act 110 to enhance the efficacy of the formulation 20. Indeed, the formulation 20 can be distributed as various standard products based on the concentrations of the different active components. Potency assays may be employed to identify how active components can be supplemented to enhance efficacy.

Stabilizers may also be added in act 110 to allow for storage of the formulation 20 at particular temperatures. For instance, the stabilizer(s) can allow the formulation 20 to be stored stably for extended periods at room temperature, i.e., approximately 70° F. Alternatively or additionally, the stabilizer(s) can allow the formulation 20 to be stored stably for extended periods at temperatures below room temperature but without requiring freezing or deep cooling of the formulation 20.

The serum 14 may also be combined in act 110 with one or more pharmaceuticals, which for instance may further assist in the eye treatment (e.g., for dry eye syndrome). For instance, the serum 14 may be combined with pharmaceuticals, such as cyclosporine. Furthermore, other substances, excipients, etc., may be added to the serum 14 in act 110 to provide the formulation 20 with particular characteristics, e.g., for storage, delivery, application, combination with other substances (e.g. pharmaceuticals), etc. For instance, the viscosity of the formulation 20 can be adjusted by adding saline, hyaluronic acid, etc.

Once any additives 18 have been added to the serum 14 in act 110, the resulting formulation 20 is stored in packaging 22 that is specially configured for delivering and optionally applying the formulation 20 to patients. In some embodiments, the resulting formulation 20 may be implemented as eye drops (e.g., for dry eye syndrome). As such, the packaging 22, for instance, may be single use containers (single dose containers) that ensure aseptic use of the eye drops as a biologic.

In some cases, the formulation 20 may be applied in a treatment with various time release techniques. For instance, as eye drops, the formulation 20 may be applied via a medium that dissolves in the eye over time and releases the eye drops in a controlled and time-dependent manner.

Although the radiation 16 is applied in act 108 to the serum as a batch for viral inactivation, FIG. 1 shows that additional radiation 24 (electron beams, gamma rays, etc.) can also be applied in act 112 to the packaged formulation 20 for viral inactivation. The type and amount of the radiation 24 applied in act 112 may be the same as or different from the radiation 16 applied in act 108. In alternative embodiments, however, viral inactivation can be achieved by applying the radiation 16 to the batch only, e.g., act 108. In other alternative embodiments, viral inactivation can be achieved by applying the radiation 16 to the packaged formulation only, e.g., act 112.

As described above, one or more active components may determine the efficacy of the formulation 20. Some active components may be susceptible to temperature degradation. As such, aspects of the process 100 may be conducted in the lowest possible temperatures and/or may employ various low temperature techniques to slow such degradation and to increase shelf life.

Although FIG. 1 may illustrate a series of acts in a particular order, it is understood that certain acts may occur more than once and/or in different orders. For instance, act 110 may occur several times to add different substances separately to the serum 14. Additionally, although the example process 100 shown in FIG. 1 may implement the formulation 20 with the serum 14 as eye drops, it is understood that the formulation 20 can be implemented in other forms of treatments, such as eye sprays or eye gels. It is also contemplated, however, that the formulation 20 may be employed as a more general excipient for the delivery of other types of pharmaceutical(s) for treatments of various disorders of the eye.

In view of the foregoing, aspects of the present disclosure can provide one or more of the following features:

- a high volume of serum for treating dry eye and/or other disorder, where the serum is pooled from a plurality of donors and processed to render viruses inactive;
- a serum-based formulation with certain (e.g., supplemented) concentrations of active components for enhanced efficacy in treatments of dry eye and/or other disorder;
- a serum-based eye formulation that can be stored stably at approximately room temperature, or at lower temperatures without requiring freezing or deep cooling;
- a serum than can include combined with one or more pharmaceuticals for treating dry eye and/or other disorder; or
- a serum-based eye formulation that is matched to the patient according to blood type.

According to aspects of the present disclosure, additional treatments (i.e., beyond dry eye treatments) may employ serum extracted from whole blood. For instance, serum-based treatments may be applied to epithelial and mucosal lesions, where the serum can improve healing and reduce healing times. Such treatments may employ particular delivery techniques and/or formulations with particular additives to improve residence time at the targeted treatment area and to optimize the benefits per unit of serum.

Serum-based treatments, for instance, may be employed for the following types of conditions (among others):

- dermatological conditions, e.g., involving ulcers (such as venous and arterial leg ulcers, diabetic foot ulcers, pressure ulcers (bedsores)), skin graft donor sites, first and second degree thermal burns, facial rejuvenation, hair loss (male pattern alopecia), vitiligo, superficial injuries, scars, cuts, abrasions, and surgical wounds.
- gynecological conditions: e.g., involving cervical ectopy, vulvar dystrophy (lichen sclerosus), reconstructive surgery for vulvar cancer, genital fistulae, premature ovarian failure, ovarian torsion, and "vaginal rejuvenation."
- ear, nose, and throat (ENT) conditions, e.g., involving endoscopic sinus surgery and vocal cord surgery and rehabilitation.
- orthopedic conditions, e.g., involving degenerative disc disease and pain, osteoarthritis, lumbar stenosis, disc prolapse, and muscle injuries.

As described above, the serum 14 can be combined with additive(s) 18 that can enhance the efficacy of the serum 14 and/or further assist in treatment of the condition (e.g., according to different mechanisms). According to further aspects of the present disclosure, formulations combine serum with additive(s) that provide anti-inflammatory and/or analgesic effects.

For instance, formulations may combine the serum with cannabinoids, which can suppress inflammatory response and act as an analgesic. Because cannabinoids are active components extracted from the plant species *Cannabis sativa*, such formulations combine a natural healing agent (serum) with a natural anti-inflammatory/analgesic.

*Cannabis* and hemp both derive from the plant species *Cannabis sativa* and contain the psychoactive component $\Delta^9$-Tetrahydrocannabinol (THC). Hemp, however, has lower concentrations of THC and higher concentrations of cannabidiol (CBD), which decreases or eliminates the psychoactive effects of THC. Thus, while the growth of *cannabis* as a narcotic is regulated, hemp is legally permitted to be grown specifically to produce industrial items, such as variety of commercial items including paper, textiles, clothing, biodegradable plastics, paint, insulation, biofuel, food, animal feed, etc. As such, CBD can be extracted from hemp and be combined as an anti-inflammatory/analgesic with serum.

Unlike CBD, other cannabinoids, such as cannabinol (CBN), cannabigerol (CBG), cannabivarin (CBV), etc., are found in smaller quantities in hemp. (Cannabinoids are generally designated as CBx). However, although the growth of hemp may be legal, the United States Food and Drug Administration (FDA) fully regulates CBD due to its use in medication. Because the distribution of the other cannabinoids (e.g., CBN, CBG, CBV) is not currently regulated in the same manner as CBD, there are advantages to implementing the other cannabinoids. For instance, CBG instead of CBD may be combined as an anti-inflammatory/analgesic with serum.

In view of the foregoing, example formulations can provide natural and non-chemically synthesized anti-inflammatory/analgesic treatments. Additionally or alternatively, example formulations can be applied for other types of treatments. For instance, a serum-based formulation may include a cannabinoid for anti-microbial effects (e.g., to treat methicillin-resistant *Staphylococcus aureus* (MRSA)).

In addition to being powerfully anti-inflammatory and strongly anti-bacterial, CBG in particular can counter psoriasis and eczema by inhibiting human keratinocyte proliferation, suppress neuropathic pain, provide neuroprotective benefits against neurodegenerative diseases, and promote neurogenesis. Thus, a formulation can combine serum with CBG for any one of the benefits above.

The examples above demonstrate how cannabinoids can be delivered in serum for treatment. In some aspects, serum is an example of a broader category of natural excipients for delivery of cannabinoids. As such, it is contemplated that cannabinoids can be implemented with other natural excipients to provide a natural and non-chemically synthesized treatment.

In general, it is contemplated that cannabinoids may be employed as an anti-inflammatory and analgesic for dry eye syndrome as well as the treatment of epithelial defects. Such use is not limited to formulations based on the serum(s) described above. Additionally, the use of cannabinoids may further call for the use of other additives. For instance, additives (such as certain adjuvants) may be employed to enhance the solubility of cannabinoids in formulations.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the present disclosure. It is also contemplated that additional embodiments according to aspects of the present disclosure may combine any number of features from any of the embodiments described herein.

What is claimed is:

1. A method, comprising:

collecting whole blood from a plurality of donors;

separating the whole blood to obtain a serum;

pooling the serum from a plurality of donors to form a pool of serum;

after pooling the serum, applying radiation to the pool of serum for viral inactivation; and after applying radiation to the pool of serum, adding one or more additives to the serum to produce eye drops, wherein the one or more additives supplement naturally occurring active components of the serum to provide supplemented concentrations of the naturally occurring active components in the eye drops, and wherein prior to separating the whole blood to obtain the serum and prior to pooling the serum, testing the whole blood collected from each donor for blood-borne pathogenic viruses.

2. The method of claim 1, further comprising selecting the whole blood from the plurality of donors according to blood type.

3. The method of claim 1, wherein separating the whole blood serum includes coagulating the whole blood and centrifuging the whole blood.

4. The method of claim 1, wherein the radiation is corpuscular radiation.

5. The method of claim 1, further comprising, after applying the radiation to the serum for viral inactivation a first time, applying additional radiation to the serum to reduce a level of active biological contaminants or pathogens.

6. The method of claim 1, wherein separating the whole blood to obtain the serum results in separation of cellular components from the serum.

7. The method of claim 1, further comprising after applying radiation to the pool of serum, adding one or more stabilizers to the serum that allow the eye drops to be stably stored at approximately 70 degrees Fahrenheit.

8. The method of claim 1, further comprising, after applying radiation to the pool of serum, adding one or more pharmaceuticals to the serum.

9. The method of claim 8, further comprising, after applying radiation to the pool of serum, adding cyclosporine to the serum.

10. The method of claim 1, further comprising, after applying radiation to the pool of serum, further adding saline and/or hyaluronic acid to the serum.

11. The method of claim 1, further comprising storing the eye drops in packaging.

12. The method of claim 11, further comprising applying additional radiation to the stored eye drops for viral inactivation, wherein applying radiation to the serum for viral inactivation is performed prior to storing the eye drops in the packaging.

13. The method of claim 11, wherein the packaging includes single dose containers.

14. The method of claim 1, further comprising combining the eye drops with a medium that dissolves in an eye over time and releases the eye drops in a controlled and time-dependent manner.

15. The method of claim 1, wherein one or more steps of the method employ low temperature to slow degradation of the whole blood, serum, and/or eye drops.

16. The method of claim 1, wherein the radiation is electromagnetic radiation.

17. The method of claim 3, further comprising:

storing the eye drops in packaging; and after storing the eye drops in the packaging, applying additional radiation to the stored eye drops for viral inactivation, wherein applying radiation to the serum for viral inactivation is performed prior to storing the eye drops in the packaging.

18. The method of claim 1, further comprising, after applying radiation to the pool of serum, adding a cannabinoid to the serum.

* * * * *